(12) United States Patent
Hart et al.

(10) Patent No.: US 7,532,985 B2
(45) Date of Patent: May 12, 2009

(54) PROCESS FOR IDENTIFYING POLYCRYSTALLINE MATERIALS BY ELECTRON DIFFRACTION

(75) Inventors: Haskell Vincent Hart, Katy, TX (US); David Robert Denley, Houston, TX (US)

(73) Assignee: Shell Oil Company, Houston, TX (US)

( * ) Notice: Subject to any disclaimer, the term of this patent is extended or adjusted under 35 U.S.C. 154(b) by 935 days.

(21) Appl. No.: 10/301,298

(22) Filed: Nov. 21, 2002

(65) Prior Publication Data

US 2003/0139890 A1 Jul. 24, 2003

Related U.S. Application Data

(60) Provisional application No. 60/333,551, filed on Nov. 27, 2001.

(51) Int. Cl.
*G06F 17/00* (2006.01)
*G01N 33/00* (2006.01)

(52) U.S. Cl. .......................................... 702/27; 423/718
(58) Field of Classification Search ........................ None
See application file for complete search history.

(56) References Cited

U.S. PATENT DOCUMENTS

| 4,553,030 | A | 11/1985 | Tokiwai et al. | 250/307 |
|---|---|---|---|---|
| 5,168,457 | A | 12/1992 | Karen et al. | 364/497 |
| 5,235,523 | A | 8/1993 | Karen et al. | 364/497 |
| 6,732,054 | B2 * | 5/2004 | Hart | 702/28 |

FOREIGN PATENT DOCUMENTS

JP 7.282.769 10/1995

OTHER PUBLICATIONS

Mighell, A.D., etc., "D-spacing/Formula Index for Compound Identification using Electron Diffraction Data" *Proceedings of the 46th Annual Meeting of the Electron Microscopy Society of America*, 912-913.
Griem, W., etc., Computer Assisted Indexing of Electron Diffraction Patterns. *Praktische Metallographic*, 14, 1977, 389-409.
Wilkes, P., etc., "Complete Indexing of Electron Diffraction Patterns by Computer" *Journal of Materials Science*, 9, 1974, 517-518.
Booth, M., etc., "A General Program for Interpreting Electron Diffraction Data" *Metallurgical Transactions*, vol. 5, Mar. 1974, 775-776.
Goehner, R.P., etc., "Computer-Aided Indexing of Transmission Elecrtron Diffraction Patterns" *Metallography*, 10, 1977, 415-424.
Mighell, A., etc., "NIST Crystallographic Databases for Research and Analysis" *Journal of Research of the National Institute of Standards and Technology*, vol. 101, No. 3, 273-280.
Anderson, R., etc., "Electron Diffraction Database", *Microscopy Society of America Bulletin*, vol. 23, No. 1, 128-137.
Lally, J.S., etc., "Computer Indexing of Electron Diffraction Patterns Including the Effect of Lattice Symmetry" *Electron Microse, X-ray Appl. Environ. Occup. Health Anal.*, Second Symposiu, Ann Arbor Society, An Arbor Michigan, 1978, 167-174.
Carr, M., etc., "A Search/Match Procedure for Electron Diffraction Data Based on Pattern Matching in Binary Bt Maps", *Powder Diffraction*, vol. 1, No. 3, 226-234.

\* cited by examiner

*Primary Examiner*—Eric S Dejong

(57) ABSTRACT

A relational database is built and used for the identification of polycrystalline solids by electron diffraction. Selected area electron diffraction (SAED) patterns (rings) produced in an electron diffractometer or a transmission electron microscope (TEM) are matched against database patterns calculated from reduced unit cells of known materials. The effects of double diffraction on electron diffraction patterns are fully incorporated into the database.

2 Claims, No Drawings

PROCESS FOR IDENTIFYING POLYCRYSTALLINE MATERIALS BY ELECTRON DIFFRACTION

This application claims the benefit of U.S. Provisional Application No. 60/333,551 filed Nov. 27, 2001, the entire disclosure of which is hereby incorporated by reference.

BACKGROUND OF THE INVENTION

Electron diffraction is an identification technique for solid crystalline phases, particles, and surfaces observed in a transmission electron microscope(TEM) or other electron diffractometer. It is often used in conjunction with elemental analysis, which is often performed by fluorescence spectrometry (called EDS for energy dispersive spectrometry) on the TEM. Together these techniques are used by scientists to identify the chemical composition and structure of unknown materials of very small size, typically 10's to 1000's of nanometers (nm) in the fields of metallurgy, catalysis, analytical chemistry, mineralogy, forensics, and environmental studies.

Identification of a known polycrystalline (meaning many crystallites in the electron beam simultaneously) phase by electron diffraction takes the form of interpreting images of concentric circles(rings) produced in the diffraction mode of the TEM. Images can be recorded on film, or more recently, collected electronically by an area detector for display on a computer monitor screen.

An identification of a previously known material (or phase) is obtained when the radii of the rings are matched to measured or calculated ring radii for a known material. As a practical matter, since ring radii also depend on instrumental parameters, a "d-spacing," which is dependent only on the crystal structure (instrument invariant) is calculated for each observed ring using Equation 1:

$$r*d = C*\lambda \quad \text{(Equation 1)}$$

wherein, r =radius of a ring in centimeters (also known as r-spacing), d=d-spacing in Angstroms, C=camera constant in millimeter-Angstroms, $\lambda$=electron wavelength in nanometers, which is determined from the electron voltage by conventional means, using the well known de Broglie Principle and related formulae.

Equation 1 is the well known application of Bragg's Law to electron diffraction (Reference 1). All references relating to the pattern of rings or concentric circles that will be alluded herein and in practice will be through the derived d-spacings (having the usual meaning to those skilled in the art of crystallography) in Angstrom(Å) units(1 Å=$10^{-10}$ meter).

Often the solutions above are not unique. In such cases, elemental analysis, for example by fluorescence spectrometry mentioned above, usually decides in favor of one or a very few possible, often chemically or structurally related, phases. Knowledge of sample history or other physical or analytical data might also be required for the final identification.

The prior art of comprehensive databases for electron diffraction is summarized in Reference 4. The Powder Diffraction File(Reference 4) of the International Centre for Diffraction Data(ICDD)is an x-ray polycrystalline diffraction database of d-spacings. Its known disadvantage(Reference 6) for use in electron diffraction is that it does not include d-spacings observed by double diffraction, because double diffraction is rare in x-ray diffraction.

Double diffraction is the phenomenon of a diffracted beam being rediffracted before exiting the crystal. The effect of this important phenomenon is that d-spacings which are unobservable("extinct") by x-radiation due to the presence of symmetry elements appear in the electron diffraction pattern of the same material. This fact makes for incomplete and uncertain matches of most electron diffraction patterns to the Powder Diffraction File.

NIST Crystal Data, currently in Release J of 1997 on CD-ROM, began in the mid-1980's as a large computer file (first available on tape) of crystallographic and related data obtained from several other original sources such as ICDD (then known as The Joint Committee for Powder Diffraction Standards—JCPDS), The Cambridge Crystallographic Centre(U.K.), The Metals Data Center (Ottawa, Canada), The Inorganic Structural Data Center (Germany), and the open literature. Today, the database contains information on 237,659 organic, inorganic, and organometallic phases (of which 79,136 are inorganic) and is available on CD-ROM from NIST or ICDD (References 2,3,4). For each phase (also called a "known material", as defined above), the data is organized into sixteen different types of several related fields each (Reference 2). The CD-ROM contains a single flat text file of these types for each phase, plus a coded literature reference file(one of the fields), and various special use files, not used here. Since d-spacings are not among the data, a reduced unit cell must first be determined from the d-spacings before searching this database. The quality and extent of typical electron diffraction patterns is inadequate to determine a unit cell, consequently the database can only be used in reverse mode. That is, guess a known material from the elemental composition of the unknown, calculate the known diffraction pattern from the database unit cell and compare to the experimental pattern. Such a process is too dependent on past experience and involves repeated calculations.

The NIST/Sandia/ICDD Electron Diffraction Database (References 3,4,6,7,8) is a collection of ring diffraction patterns(mostly calculated from NIST Crystal Data, but also obtained from the Powder Diffraction File and related phase information along with search software(EDSEARCH) and utility programs for electron diffraction. It is available through the ICDD. Developed in the mid-1980's, the system was written for a PC with limited disk storage (approximately 10 Mb), limited memory (approximately 640K), limited other general use PC software(e.g. for relational databases), and relatively slow speed(less than 50 MHz) in mind. Consequently, it sacrifices user convenience and flexibility for code optimization and data storage considerations. The results from the EDSEARCH option must be examined by hand in great detail for realistic solutions("candidate materials") to the problem. Usually, the correct solution(s) are found among many other solutions which are equally or nearly equally ranked by its "Figure of Merit" (FOM) index, defined below. Recommended values for FOM minimum and number of input rings are 80 and six, respectively.

The FOM is defined in EDSEARCH as:

$$\text{FOM} = 200 \sum_{i=1}^{N} W_i / \{N(N+1)\} \quad \text{(Equation 2)}$$

wherein N=number of experimental r-spacings, Wi=weighting factor, either N+1−i or zero, depending on whether the i-th R-spacing is a hit or a miss. R-spacings are numbered consecutively beginning with the smallest. Interpretation of the FOM is as follows. N(N+1)/2 is the sum of N consecutive integers. Hence the formula is a percentage of this total achieved by r-spacings which are "hits" to the database. Shortcomings of this formula are that the lowest-r (highest-d) is most heavily weighted, so that if these are weak or absent due to amorphous or other background the FOM may be set too high. Also, it gives no consideration to r-spacings in the database which are not observed experimentally. Low symmetry phases with large unit cells may easily match a few experimental r-spacings, but be poor overall fits, even though the FOM could be the maximum 100.

Another disadvantage of EDSEARCH is the conceptual hinderance of dealing with output in r-spacings instead of d-spacings (See Equation 1). Experience with diffraction patterns obtained by different means involves comparing the crystal parameters, the d-spacings, not the r-spacings. The d-spacings are instrument independent and are remembered by practicioners to some degree for common materials from problem to problem. This facilitates interpretation of output reports, and recognition of familiar phases.

The NIST/Sandia/ICDD Electron Diffraction Database does not fully utilize the power of the modern PC and modern software to make the task of rings interpretation as simple as possible for the electron microscopist. It does not allow experimental error input, and it does not properly account for "double diffraction", both of which can add to the number of potential solutions to sort through. It has no interface to other desktop software commonly in use for further customizing, sorting, filtering, processing, or reporting results. And most importantly, it does a poor job of ranking its many potential solutions, making interpretation of output very difficult.

NIST/Sandia/ICDD Electron Diffraction Database claims to account for the most common type(only) of double diffraction by doubling the six(arbitrarily) lowest r-spacings and adding these to the experimental pattern for matching against the reference pattern in the database. In this way either the original line or its R-double(or d-half) need match the database for a hit. This is assuming the reference pattern is from the x-ray PDF or calculated as an x-ray pattern from the full symmetry unit cell(properly accounting for x-ray extinctions). The addition of the extra six lines, some or all of which may be superfluous, make the search/match less robust.

The final database is available in book form only, the Elemental and Interplanar Spacing Index (EISI). (Reference 9) On one line per phase it contains an alphabetical listing of elements(by symbol) and the highest ten d-spacings in decreasing order. The contention of the authors is that the elemental composition and the highest d-spacings are sufficient for quick manual search/match in most cases. However, the EISI does not include the effects of double diffraction. We did not use this index, but its use is discussed elsewhere (Reference 4).

SUMMARY OF THE INVENTION

The present invention provides a method for creating a searchable database of polycrystalline electron diffraction data comprising: (a) creating tables within a relational database, said tables comprising Code Ring data, Formula data, and Element data; wherein said Code Ring data includes information relating to the d-spacings of polycrystalline materials, said Formula data includes information relating to the chemical formulae of said polycrystalline materials, and said Element data includes information relating to the presence of elements in said polycrystalline materials of high atomic number; (b) creating at least one macro for performing searches using said tables; said at least one macro including the steps of: (i) requesting input data relating to observed d-spacings, experimental error limits, and anticipated atomic numbers of an experimental sample; (ii) comparing said input data with the data in said tables and calculating a Figure of Merit (FOM) such that:

$$FOM = (\text{matching } d\text{-spacings}) - (\text{missing } d\text{-spacings});  \quad\text{(Equation 3)}$$

and (iii) generating at least one report listing in descending order the polycrystalline materials that have the highest FOM.

The invention further provides a method for classifying polycrystalline electron diffraction data obtained from an experimental sample, comprising: (a) generating a relational database comprising: (i) at least three tables holding Code Ring data, Formula data, and Element data, respectively; wherein said Code Ring data includes information relating to the d-spacings of polycrystalline materials, said Formula data includes information relating to the chemical formulae of said polycrystalline materials, and said Element data includes information relating to the presence of elements in said polycrystalline materials of high atomic number; (ii) at least one macro for performing searches using said tables; said at least one macro including the steps of (1) requesting input data relating to observed d-spacings, experimental error limits, and anticipated atomic numbers of an experimental sample; (2) comparing said input data with the data in said tables and calculating a Figure of Merit (FOM) such that:

$$FOM = (\text{matching } d\text{-spacings}) - (\text{missing } d\text{-spacings});$$

(3) generating at least one report listing in descending order the polycrystalline materials that have the highest FOM; and (b) using said macro of said relational database to enter electron diffraction data obtained from said experimental sample and to obtain said at least one report.

The invention is further directed to a relational database for classifying polycrystalline electron diffraction data obtained from an experimental sample, said database comprising: (a) at least three tables holding Code Ring data, Formula data, and Element data, respectively; wherein said Code Ring data includes information relating to the d-spacings of polycrystalline materials, said Formula data includes information relating to the chemical formulae of said polycrystalline materials, and said Element data includes information relating to the presence of elements in said polycrystalline materials of high atomic number; (b) at least one macro for performing searches using said tables; said at least one macro including the steps of: (i) requesting input data relating to observed d-spacings, experimental error limits, and anticipated atomic numbers of an experimental sample; (ii) comparing said input data with the data in said tables and calculating a Figure of Merit (FOM) such that:

$$FOM = (\text{matching } d\text{-spacings}) - (\text{missing } d\text{-spacings});$$

and (iii) generating at least one report listing in descending order the polycrystalline materials that have the highest FOM.

The invention allows an electron microscopist with little or no training in crystallography, and with only elementary training in common personal computer(PC) software tools to identify the substance or substances which produce a polycrystalline electron diffraction pattern from among as wide as possible a set of "knowns," for example all inorganic materials in the NIST Crystal Data file(Version J, 1997). The tasks can be accomplished in less than 14 seconds search time (the common limit of human patience in such matters).

DETAILED DESCRIPTION OF THE INVENTION

The application and use of this invention requires the measurements and calculations as described in BACKGROUND OF THE INVENTION to produce d-spacings for the search/match identification, which is the basis of the invention. Although, obtaining the d-spacings is outside the scope of this invention, they generally can be obtained as follows. For a polycrystalline sample, an electron diffraction pattern of concentric circles(rings) is obtained on either (1) an electron diffractometer or (2) a transmission electron microscope (TEM) equipped with a diffraction mode, and is recorded using either: (a) a fluorescent screen and photographic film or (b) an electronic detector capable of converting diffracted electron impulses in two dimensional space to electronic signals which are converted, with their spacial positions, to digital form and stored in a computer file.

Accordingly, either: (a) the radii of the concentric circles on the film are measured and together with the electron voltage or electron wavelength and the camera length (the distance between sample and recorder) of the diffractometer or TEM are used to calculate the d-spacings of the polycrystalline sample in Angstrom units(Å), or b) the electronic file of converted signal impulses and together with the electron voltage or electron wavelength and the camera length of the diffractometer or TEM is processed through computer programs or other calculations to produce the d-spacings of the polycrystalline sample in Angstrom units.

In the present embodiment, application of this invention proceeds through the following steps required to run a search/match of a polycrystalline electron diffraction pattern:

(1) Open the macro macRINGS2.

(2) In Input box 1: From the keyboard, enter a symbol of an element known to be present (Z>10). Repeat for each element (Z>10) known to be present. No unspecified heavy elements will be allowed in the solution, and all specified elements must be present. This requires a complete x-ray (or other comparable elemental) analysis. Enter "0" (zero) to stop adding elements. All elements with Z<=10 cannot be entered and are considered to be possibly present(i.e., any combination of these light elements, including none, is allowed).

(3) In Input box 2: Enter the experimental error limit on d-values, "err. d," in %(recommended default input 1.5). A match occurs when a database d-value is within this percent of the experimental value, i.e. when $$(100-\text{err. d})*d(\text{exptl.}) \leq [100d(\text{database})] \leq (100+\text{err. d})*d(\text{exptl.}).$$

(4) In Input box 3: Enter "1" for file input of R-values(in cm), or "0" (zero) for keyboard input of d-values (in Angstroms).

(5) (a) For "1" in box 3:

Input box 4a: Enter a complete path to a text input file (previously generated) with five header rows followed by one R-value(ring radius) per row.

Example: d:\electron diffraction\filename.txt.

Input box 4b: Enter the camera length in mm(default value 250).

Input box 4c: Enter the electron wavelength in nm(default value 0.00197).

OR (b) For 0(zero) in box 3:

Input box 5: Enter a d-value in Å (Angstroms). Continue until all d-values are entered. Enter a 0(zero) to halt input of d-values.

Input box 6: Enter the minimum number of required d-value matches. About 80% of the total number of experimental d-values >0.8 A is a recommended minimum for single phase problems, use less for multiphase problems.

Output: A "summary table of candidate materials," rpt Summary, is opened automatically by the macro macRings2 and is comprised of, for each candidate material:
(i) a unique index code(hereinafter called the "CODE") with which other information, not in the output, may be obtained from another database or other source,
(ii) a chemical formula(hereinafter called "FORMULA"),
(iii) a Figure of Merit, FOM, as defined by Equation 3, by which to judge the relative likelihood of the candidate materials to be the actual sample material with the measured input d-spacings,
(iv) the number of matching d-spacings common to input d-spacings and database d-spacings within the input error limits,
(v) the number of missing d-spacings, between the maximum input d-spacing plus the error limit and 0.8 Angstroms, which are present in the database but absent in the input,
(vi) the difference between the number in (iv) minus the number in (v), which is defined as the FOM in (iii).

The "summary table of candidate materials" is ordered (top to bottom) according to the FOM (highest to lowest).

A "table of details for each candidate material," rptDetails, is opened next and is comprised of, for each candidate material,
(i) the FOM
(ii) the CODE
(iii) the FORMULA
(iv) the list of all database d-spacings, one per line,
(v) the matching input d-spacings, each on the same line as the matching database d-spacing or d-spacings.

The candidate materials in rptDetails are ordered (top to bottom) in the same order as the rptSummary. Within each candidate material, database d-spacings are ordered (top to bottom) by decreasing d-spacing value in Angstroms.

EXAMPLE 1A

NiO

Table 1 prints the raw data file of R-values (Equation 1) from a known NiO sample. The RINGS search routine reads this electronic file and first calculates d-values from R-values by Equation 1, then selects only those d-values >0.8 Å for the search. These are the first nine values only (in this case d=2.41, 2.08, 1.46, 1.24, 1.20, 1.04, 0.93, 0.84, 0.80 Å). Other keyboard input includes the elemental symbol Ni (oxygen has too low an atomic number to be observed in x-ray analysis, Z<10), an error limit 1.5% on d, and the number of required d-matches, seven here. Table 2 prints the summary output, which is contained in the database report, rptSummary. Table 3 contains the details of each solution in the report rptDetails. The first seven solutions with highest FOMs are indistinguishable without further investigation of d-values <0.8 Å. All other solutions with FOM<6 are unlikely, due to the large number of unobserved d-values. The FOM break-point between likely and unlikely solutions is obvious. Nine of fourteen solutions are oxides of nickel, all but one of the nine have formula NiO. Slight variations in diffraction patterns and even stoichiometry($Ni_2O_3$) are the result of known isomorphous structures with differing amounts of $Ni^{+2}$ and $Ni^{+3}$ ions (with metal ion vacancies to match the number of $Ni^{+3}$ ions). As a group, the nickel oxide formulas match better than the others. In summary, one is quite confident of having a nickel oxide, most likely one close to the formula NiO as represented by the first seven solutions.

EXAMPLE 1B

NiO by EDSEARCH

EDSEARCH output for the NiO problem described above contained 133 possible solutions, of which 11 are nickel oxides (compared to only 14 and nine, respectively, for Example 1A from RINGS above). EDSEARCH required only THREE d-matches (chosen by the software—not the user) for the recommended "Figure of Merit" minimum of 80/100. In fact, most solutions have "FOM: 100," and most of these are poor matches, so the FOM is not very discriminating. The output lists r-spacings rather than the more universal d-value(Equation 1). All nine nickel oxide solutions found in Example 1A are included in the 11 nickel oxide solutions from EDSEARCH, so there is some agreement between the two approaches.

EXAMPLE 2A

TlCl

Tables 4 and 5 print the output of a TlCl(thallous chloride) search with eight experimental d-values(six required matches), entered from the keyboard: 3.82, 2.73, 2.22, 1.93, 1.72, 1.57, 1.21, 1.02 A. RINGS gave only four possile solutions, two indistinguishable TlCl phases with FOM=−2, and two similar $TlClO_4$ phases with FOM=−6. By examination of rptDetails, the TlCl phases are clearly preferred, because of the match of the highest five d-values. In this example the FOM's were negative primarily because the experimental data contained only the strongest eight lines out to 1.02 A, whereas database d's went to 0.8 A. However, the ordering of solutions by decreasing FOM, again put the best solutions on top of rptSummary with a clear FOM break point.

EXAMPLE 2B

TlCl by EDSEARCH

The output EDSEARCH for TlCl contained 21 possible solutions, of which three are TlCl(compared to four and two, respectively, for RINGS—Example 2A). Included among the 21 solutions are the two TlCl and two $TlClO_4$ phases found in the RINGS search in Example 2A. Only TWO d-spacing matches were required (software determined), though the minimum FOM was set to 80/100. Most of the incorrect phases were poor overall matches.

In another embodiment, the present invention also builds a relational database from the inorganic materials contained in NIST Crystal Data, Version J, 1997, by incorporating, for each material, the CODE(to uniquely reference each material), the FORMULA (for common recognition and to obtain the elements present), and the reduced unit cell (for the calculation of d-spacings of each material—stored as 100D values). Further, the present embodiment uses Microsoft Access 97 to build the relational database. However, other sources of identification numbers, chemical formulas, and reduced unit cells for inorganic materials, as well as other commercial database products may be easily substituted in other embodiments of this invention by those skilled in the arts of crystallography and database management.

The relational database of known materials consists of a collection of relational database "objects," which are:

(a) program "modules," in this embodiment written in Microsoft Visual Basic for Applications(VBA) program code, (b) "tables", (c) "queries" of the tables in (b) and other tables produced by the queries, (d) "macros" (combinations of database commands, involving tables, queries, modules, and other macros) and, (e) "reports, wherein all "modules," "tables," "queries," "macros," and "reports" have the common meanings usually associated with a "relational database," in this embodiment Microsoft ACCESS 97.

In one such embodiment the "database of known materials" contains:

(a) the following tables, wherein each table contains one or more records for each "known material," with a "record" being one line of the table (the usual definition associated with a relational database table):

(i) Database Table tblICodeRings. CODE and 100*(d-spacing, in Angstroms), as an integer, hereinafter referred to as "100D," for all d-spacings >0.8 Å or the 25 largest such d-spacings, whichever is fewer, the CODE is an index used to retrieve other information on candidate materials, for example through additional relational database tables, queries, macros, and reports. It connects all the data in the following tables.

(ii) Database Table tblIFormulas. CODE and FORMULA, (iii) Database Table tblIElements. CODE, N(1), N(2), N(3), N(4), N(5), N(6), N(7) where N(1) to N(7) are the sums of numeric element identifiers for elements with atomic numbers 1-15, 16-30, 31-45, 46-60, 61-75, 76-90, 91-105, respectively, and each numeric element identifier is 2 raised to the power: Z-15*(i-1), where, i is the index of the sums of numeric element identifiers, N(i), ranging from i=1 to i=7 (above), and Z is the atomic number of each element present, and (b) a macro, RINGS2, which controls the entire search/match procedure, from input to output, and which contains the following separate steps:

(i) Open Module modInputE2
(ii) Run Code E2( )
(iii) Close Module modInputE2
   Element symbols are input
   Values of N(i) are calculated according to a(iii).
(iv) Open Query qryELE2
(v) Close Query qryELE2
   Table tblIElements is queried for matching values of N(i)
   A table, tblELE, of CODE and matching N(1)-N(7) values is produced.
(vi) Open Module modERRORS
(vii) Run Code ERRDFile( )
(viii) Close Module modERRORS
   % error in d is input and written to a file.
(ix) Run Macro macDvalues2
(x) Close Macro macDvalues2
   d-spacings are input through keyboard or calculated from an input file of r-spacings and written to a file.
(xi) Open Query qryDvalues
(xii) Close Query qryDvalues Tables tblELE, tblICodeRings, and tblIFormulas are queried for materials with matching elements and d-spacings within the input % error of(b)(viii).

An output table of materials, tblDvalues, is produced, consisting of CODE, FORMULA, and 100D for for each.

(xiii) Open Query qryDcount
(xiv) Close Query qryDcount

The table tblDvalues is queried for the number of matching d-spacings for each material.

A table tblDcountsum is produced, consisting of CODE and number of matching d-spacings for each material.

(xv) Open Query qryFinalDsorted2
(xvi) Close Query qryFinalDsorted2

Tables tblDcountsum, tblICodeRings, and tblDvalues are queried and consolidated by CODE.

A table tblfinalDsorted is produced, in which number of matching d-spacings, CODE, FORMULA, database d-spacing, and matching input d-spacing (where appropriate) are entered in records, and sorted by number of matching d-spacings and CODE for each material. Only materials with the minimum number of reqiuired matching d-spacings are entered.

(xvii) Open Query qryMismatches
(xvii) Close Query qryMismatches

Tables tblDvalues, tblDcountsum, and tblICodeRings are queried and consolidated.

A table tblMismatches is produced consisting of CODE, number of observed d-spacings, and all database d-spacings for each candidate material.

(xix) Delete Table tblMismatches2

Deletes a previous version of the table, if present in the database.

(xx) Open Query qryMismatches2
(xxi) Close Query qryMismatches2

Table tblMismatches is queried, and database 100D values are counted for each material A table tblMismatches2 is produced consisting of, for each candidate material, CODE, number of matching d-spacings, and Number of database 100D values.

(xxii) Delete Table tblMismatches3

Deletes a previous version of the table, if present in the database.

(xxiii) Open Query qryMismatches3
(xxiv) Close Query qryMismatches3 tblMismatches is queried and a new table, tblMismatches3, is produced consisting of, for each candidate material, CODE, 100D, for d less than the maximum input d+the error limit(the input range).

(xxv) Delete Table tblMismatches4

Deletes a previous version of the table, if present in the database.

(xxvi) Open Query qryMismatches4
(xxvii) Close Query qryMismatches4 tblMismatches3 is queried, and the number of database 100D values in the input range of (b)(xxiv) is counted for each candidate material.

A table tblMismatches4 is produced, consisting of, for each candidate material, CODE, and number of database 100D values in the input range.

(xxviii) Delete Table tblMatchingDs deletes a previous version of the table, if present in the database.

(xxix) Open Query qryMatchingDs
(xxx) Close Query qryMatchingDs

The tables tblfinalDsorted and tblMismatches4 are queried, and a table, tblMatchingDs is produced, consisting of, for each candidate material, CODE, FORMULA, number of matching d-spacings(A) in the database, number of 100D values in the database in the input range(B), number of missing d-spacings(B-A), FOM Equation 3.

(xxxi) Open Report rptSummary

The "summary table of candidate materials" described in Claim 4.($a$) is produced.

(xxxii) Delete Table tblELE

Deletes the table, in preparation for the next search.

(xxxiii) Delete Table tblDcountsum

Deletes the table, in preparation for the next search.

(xxxiv) Delete Table tblMismatches

Deletes the table, in preparation for the next search.

(xxxv) Stop Macro, and (c) the macro macDvalues2(b)(ix) and (b)(x) consists of the separate steps:

(i) Open Module modDfile
(ii) Run Code InputDs( )
(iii) Stop Macro.

For the database table tblICodeRings in (a)(i), the d-spacings for each known material are computed by varying the Miller indices(h,k,l) from (0,0,0) to (a/0.8, b/0.8, c/0.8), in separate unit integer increments, and with the reduced unit cell parameters $a,b,c,\alpha,\beta,\gamma$(References 2,3,4), considered as a triclinic cell, and by using the standard triclinic crystallographic formula(Reference 5). The d-spacings so calculated are multiplied by 100 and rounded off to the nearest integer and converted to integer data format, after which they are sorted highest to lowest, with redundancies deleted, and limited to the 25 largest above 0.8 Å, which are written to a file along with the corresponding CODE. This process is repeated for each known material with a reduced unit cell. A single computer file of such d-spacings, plus the CODE for each known material, is read into the relational database table tblICodeRings described in (a)(i).

The database table tblIFormulas (a)(ii) is produced by reading an external datafile containing records of CODE and FORMULA for each known material into the table.

The database table tblIElements in (a)(iii) is produced by reading a datafile of CODE, N(1), N(2), N(3), N(4), N(5), N(6), N(7) for each known material into the database table. This preliminary datafile is produced by searching each FORMULA for each of the 105 chemical symbols, assigning appropriate numeric indicators for each element symbol found according to (a)(iii), and totaling these numeric indicators within each atomic number range(1 through 7) as in (a)(iii).

The CODE for each known material as used above is consistent for each known material throughout the relational database, so that it is possible to relate it to the elements present, the FORMULA, and all stored 100D values in a unique manner. Similarly, in the macro macRINGS2 the CODE for each known material is used consistently throughout all queries, intermediate tables, macros, modules, and reports.

Illustrative examples of method for identifying polycrystalline materials from electron diffraction patterns, relevant crystallographic theory and application, and the techniques of electron diffraction can be found in the following literature and the description thereof are herein incorporated by reference:

1. Andrews, K. W., Dyson, D. J., and Keown, S. R., Interpretation of Electron Diffraction Patterns, Second Edition, Adam Hilger, London, 1971, esp. pp. 15, 26-27.

2. Stalick, Judith K., and Mighell, Alan D.(1986), Crystal Data, Version 1.0 Database Specifications, NBS Technical Note 1229, National Bureau of Standards.
3. Mighell, Alan, and Karen, Vicky Lynn(1996), NIST Crystallographic Databases for Research and Analysis, Journal of Research of the National Institute of Standards and Technology, v. 101, No. 3, 273-280.
4. Anderson, Ron, Mighell, Alan D., Karen, Vicky Lynn, Jenkins, Ron, And Carr, Martin J.(1993), Electron Diffraction Databases, Microscopy Society of America Bulletin, v. 23, No. 1, 128-137.
5. Kasper, John S. and Lonsdale Kathleen, eds.(1972), International Tables for X-ray Crystallography, V. II, 3rd ed., Knoch Press, Birmingham, U.K., 106.
6. Carr, Martin J., Chambers, William F., and Melgaard, David(1986), A Search/Match Procedure for Electron Diffraction Data Based on Pattern Matching in Binary Bit Maps, Powder Diffraction, v. 1, No.3, 226-234.
7. Carr, M. J., Chambers, W. F., Melgaard, D. K., Himes, V. L., Stalick, J. K., Mighell, A. D.(1987), NBS/Sandia/ICDD Electron Diffraction Database, National Technical Information Service, U. S. Department of Commerce.
8. Carr, M. J., Chambers, W. F., Melgaard, D., Himes, V. L., Stalick, J. K., and Mighell, A. D.(1989), NIST/Sandia/ICDD Electron Diffraction Database: A Database for Phase Identification by Electron Diffraction, J. Res. Nat. Inst. Std. Tech., v. 94, no. 1, 15-20.
9. Mighell, A. D., Himes, V. L., Anderson, R., and Carr, M. J.(1988), D-spacing/Formula Index for Compound Identification using Electron Diffraction Data, Proc. Ann. Meeting Electron Miscros. Soc. Am., 46th, 912-913.

BRIEF DESCRIPTION OF THE TABLES

Table 1. Input Data File for NiO
Table 2. Summary Output from NiO Search
Table 3. Detailed Output from NiO Search
Table 4. Summary Output from TlCl Search
Table 5. Detailed Output from TlCl Search

TABLE 1

Input Data File for NiO.
CL = 250 mm; Lambda = 0.00197 nm

| |
|---|
| 0.204750 |
| 0.237250 |
| 0.336375 |
| 0.396500 |
| 0.411125 |
| 0.474500 |
| 0.531375 |
| 0.583375 |
| 0.617500 |
| 0.672750 |

TABLE 2

Summary Output from NiO Search.

| FOM | CODE | Formula | matching d's | d's in range | missing d's |
|---|---|---|---|---|---|
| 10 | 022186 | NiO | 11 | 12 | 1 |
| 10 | H727456 | NiO | 11 | 12 | 1 |
| 9 | 024133 | NiO | 9 | 9 | 0 |
| 8 | 022487 | NiO | 9 | 10 | 1 |
| 8 | 700611 | NiO | 9 | 10 | 1 |
| 8 | 804006 | NiO | 9 | 10 | 1 |
| 6 | 021989 | NiO | 8 | 10 | 2 |

TABLE 2-continued

Summary Output from NiO Search.

| FOM | CODE | Formula | matching d's | d's in range | missing d's |
|---|---|---|---|---|---|
| 1 | 1728035 | NH4NiF3 | 7 | 13 | 6 |
| -3 | 025859 | Ni2O3 | 9 | 21 | 12 |
| -5 | 111370 | NiO | 8 | 21 | 13 |
| -6 | F722306 | Ni(HCO3)2 | 7 | 20 | 13 |
| -7 | F722364 | Li2NiF4 | 7 | 21 | 14 |
| -9 | 024788 | NiOOH | 7 | 23 | 16 |
| -9 | F946030 | NiOOH | 7 | 23 | 16 |

TABLE 3

Detailed Output from NiO Search.

| FOM: | 10 |
|---|---|
| CODE: | 022186 |
| Formula: | NiO |
| d-value | match |

| d-value | match |
|---|---|
| 2.41 | 2.40 |
| 2.09 | 2.07 |
| 1.48 | 1.46 |
| 1.47 | 1.46 |
| 1.26 | 1.24 |
| 1.21 | 1.19 |
| 1.2 | 1.19 |
| 1.04 | 1.03 |
| 0.96 | |
| 0.93 | 0.92 |
| 0.85 | 0.84 |
| 0.8 | 0.79 |

| CODE: | H727456 |
|---|---|
| Formula: | NiO |
| d-value | match |

| d-value | match |
|---|---|
| 2.41 | 2.40 |
| 2.09 | 2.07 |
| 1.48 | 1.46 |
| 1.47 | 1.46 |
| 1.26 | 1.24 |
| 1.21 | 1.19 |
| 1.2 | 1.19 |
| 1.04 | 1.03 |
| 0.96 | |
| 0.93 | 0.92 |
| 0.85 | 0.84 |
| 0.8 | 0.79 |

| FOM: | 9 |
|---|---|
| CODE: | 024133 |
| Formula: | NiO |
| d-value | match |

| d-value | match |
|---|---|
| 2.37 | 2.40 |
| 2.05 | 2.07 |
| 1.45 | 1.46 |
| 1.24 | 1.24 |
| 1.18 | 1.19 |
| 1.03 | 1.03 |
| 0.94 | 0.92 |
| 0.92 | 0.92 |
| 0.84 | 0.84 |

| FOM: | 8 |
|---|---|
| CODE: | 022487 |
| Formula: | NiO |
| d-value | match |

| d-value | match |
|---|---|
| 2.41 | 2.40 |
| 2.09 | 2.07 |
| 1.47 | 1.46 |
| 1.26 | 1.24 |

TABLE 3-continued

Detailed Output from NiO Search.

| d-value | match |
|---|---|
| 1.2 | 1.19 |
| 1.04 | 1.03 |
| 0.96 | |
| 0.93 | 0.92 |
| 0.85 | 0.84 |
| 0.8 | 0.79 |

CODE: 700611
Formula: NiO

| d-value | match |
|---|---|
| 2.41 | 2.40 |
| 2.09 | 2.07 |
| 1.47 | 1.46 |
| 1.26 | 1.24 |
| 1.2 | 1.19 |
| 1.04 | 1.03 |
| 0.96 | |
| 0.93 | 0.92 |
| 0.85 | 0.84 |
| 0.8 | 0.79 |

CODE: 804006
Formula: NiO

| d-value | match |
|---|---|
| 2.41 | 2.40 |
| 2.09 | 2.07 |
| 1.47 | 1.46 |
| 1.26 | 1.24 |
| 1.2 | 1.19 |
| 1.04 | 1.03 |
| 0.96 | |
| 0.93 | 0.92 |
| 0.85 | 0.84 |
| 0.8 | 0.79 |

FOM: 6
CODE: 021989
Formula: NiO

| d-value | match |
|---|---|
| 2.42 | 2.40 |
| 2.09 | 2.07 |
| 1.48 | 1.46 |
| 1.26 | 1.24 |
| 1.21 | 1.19 |
| 1.05 | 1.03 |
| 0.96 | |
| 0.94 | 0.92 |
| 0.85 | 0.84 |
| 0.81 | |

FOM: 1
CODE: I728035
Formula: NH4NiF3

| d-value | match |
|---|---|
| 14.35 | |
| 7.17 | |
| 4.78 | |
| 4.36 | |
| 4.18 | |
| 3.73 | |
| 3.59 | |
| 3.22 | |
| 2.87 | |
| 2.77 | |
| 2.52 | |
| 2.48 | |
| 2.4 | 2.40 |
| 2.39 | 2.40 |
| 2.38 | 2.40 |
| 2.23 | |
| 2.18 | |
| 2.16 | |
| 2.1 | 2.07 |
| 2.09 | 2.07 |
| 2.06 | 2.07 |
| 2.05 | 2.07 |
| 1.99 | |
| 1.89 | |
| 1.86 | |

FOM: −3
CODE: 025859
Formula: Ni2O3

| d-value | match |
|---|---|
| 4.18 | |
| 2.96 | |
| 2.41 | 2.40 |
| 2.09 | 2.07 |
| 1.87 | |
| 1.71 | |
| 1.48 | 1.46 |
| 1.39 | |
| 1.32 | |
| 1.26 | 1.24 |
| 1.21 | 1.19 |
| 1.16 | |
| 1.12 | |
| 1.04 | 1.03 |
| 1.01 | |
| 0.99 | |
| 0.96 | |
| 0.93 | 0.92 |
| 0.91 | |
| 0.89 | |
| 0.85 | 0.84 |
| 0.84 | 0.84 |
| 0.82 | |

FOM: −5
CODE: 111370
Formula: NiO

| d-value | match |
|---|---|
| 4.17 | |
| 2.95 | |
| 2.41 | 2.40 |
| 2.09 | 2.07 |
| 1.86 | |
| 1.7 | |
| 1.47 | 1.46 |
| 1.39 | |
| 1.32 | |
| 1.26 | 1.24 |
| 1.2 | 1.19 |
| 1.16 | |
| 1.11 | |
| 1.04 | 1.03 |
| 1.01 | |
| 0.98 | |
| 0.96 | |
| 0.93 | 0.92 |
| 0.91 | |
| 0.89 | |
| 0.85 | 0.84 |
| 0.83 | |
| 0.82 | |

FOM: −6
CODE: F722306
Formula: Ni(HCO3)2

| d-value | match |
|---|---|
| 5.93 | |
| 4.19 | |
| 3.42 | |
| 2.96 | |
| 2.65 | |
| 2.42 | 2.40 |
| 2.24 | |
| 2.1 | 2.07 |

TABLE 3-continued

Detailed Output from NiO Search.

| d-value | match |
|---|---|
| 1.98 | |
| 1.87 | |
| 1.79 | |
| 1.71 | |
| 1.64 | |
| 1.53 | |
| 1.48 | 1.46 |
| 1.44 | |
| 1.4 | |
| 1.36 | |
| 1.33 | |
| 1.29 | |
| 1.26 | 1.24 |
| 1.24 | 1.24 |
| 1.21 | 1.19 |
| 1.19 | 1.19 |
| 1.16 | |

| | |
|---|---|
| FOM: | −7 |
| CODE: | F722364 |
| Formula: | Li2NiF4 |
| d-value | match |

| d-value | match |
|---|---|
| 4.76 | |
| 4.12 | |
| 2.91 | |
| 2.49 | |
| 2.38 | 2.40 |
| 2.06 | 2.07 |
| 1.89 | |
| 1.84 | |
| 1.68 | |
| 1.59 | |
| 1.46 | 1.46 |
| 1.39 | |
| 1.37 | |
| 1.3 | |
| 1.26 | 1.24 |
| 1.24 | 1.24 |
| 1.19 | 1.19 |
| 1.15 | |
| 1.14 | |
| 1.1 | |
| 1.07 | |
| 1.03 | 1.03 |
| 1.01 | |
| 1 | |
| 0.97 | |

| | |
|---|---|
| FOM: | −9 |
| CODE: | 024788 |
| Formula: | NiOOH |
| d-value | match |

| d-value | match |
|---|---|
| 6.88 | |
| 3.44 | |
| 2.43 | 2.40 |
| 2.38 | 2.40 |
| 2.29 | |
| 2.21 | |
| 2.1 | 2.07 |
| 1.88 | |
| 1.77 | |
| 1.72 | |
| 1.58 | |
| 1.49 | |
| 1.41 | |
| 1.38 | |
| 1.33 | |
| 1.3 | |
| 1.26 | 1.24 |
| 1.22 | |
| 1.21 | 1.19 |
| 1.2 | 1.19 |
| 1.19 | 1.19 |
| 1.17 | |
| 1.15 | |
| 1.14 | |
| 1.13 | |

| | |
|---|---|
| CODE: | F946030 |
| Formula: | NiOOH |
| d-value | match |

| d-value | match |
|---|---|
| 4.66 | |
| 2.55 | |
| 2.43 | 2.40 |
| 2.33 | |
| 2.08 | 2.07 |
| 1.9 | |
| 1.58 | |
| 1.55 | |
| 1.5 | |
| 1.49 | |
| 1.45 | 1.46 |
| 1.42 | |
| 1.29 | |
| 1.27 | |
| 1.26 | 1.24 |
| 1.23 | 1.24 |
| 1.21 | 1.19 |
| 1.17 | |
| 1.14 | |
| 1.09 | |
| 1.08 | |
| 1.04 | 1.03 |
| 0.99 | |
| 0.98 | |
| 0.97 | |

TABLE 4

Summary Output from TlCl Search

| FOM | CODE | Formula | matching d's | d's in range | missing d's |
|---|---|---|---|---|---|
| −2 | 021948 | TlCl | 8 | 18 | 10 |
| −2 | 021949 | TlCl | 8 | 18 | 10 |
| −6 | 024199 | TlClO4 | 9 | 24 | 15 |
| −6 | 024205 | TlClO4 | 9 | 24 | 15 |

TABLE 5

Detailed Output from TlCl Search

| | |
|---|---|
| FOM = | (matching d's) − (missing d's) |
| FOM: | −2 |
| CODE: | 021948 |
| Formula: | TlCl |
| d-value | match |

| d-value | match |
|---|---|
| 3.83 | 3.82 |
| 2.71 | 2.73 |
| 2.21 | 2.22 |
| 1.92 | 1.93 |
| 1.71 | 1.72 |
| 1.56 | 1.57 |
| 1.35 | |
| 1.28 | |
| 1.21 | 1.21 |
| 1.15 | |
| 1.11 | |
| 1.06 | |
| 1.02 | 1.02 |
| 0.96 | |
| 0.93 | |
| 0.9 | |
| 0.88 | |
| 0.86 | |

TABLE 5-continued

Detailed Output from TlCl Search

| | |
|---|---|
| CODE: | 021949 |
| Formula: | TlCl |
| d-value | match |
| 3.84 | 3.82 |
| 2.72 | 2.73 |
| 2.22 | 2.22 |
| 1.92 | 1.93 |
| 1.72 | 1.72 |
| 1.57 | 1.57 |
| 1.36 | |
| 1.28 | |
| 1.21 | 1.21 |
| 1.16 | |
| 1.11 | |
| 1.07 | |
| 1.03 | 1.02 |
| 0.96 | |
| 0.93 | |
| 0.91 | |
| 0.88 | |
| 0.86 | |
| FOM: | −6 |
| CODE: | 024199 |
| Formula: | TlClO4 |
| d-value | match |
| 4.4 | |
| 3.81 | 3.82 |
| 2.7 | 2.73 |
| 2.69 | 2.73 |
| 2.3 | |
| 2.2 | 2.22 |
| 1.91 | 1.93 |
| 1.75 | |
| 1.7 | 1.72 |
| 1.56 | 1.57 |
| 1.47 | |
| 1.35 | |
| 1.29 | |
| 1.27 | |
| 1.21 | 1.21 |
| 1.16 | |
| 1.15 | |
| 1.1 | |
| 1.07 | |
| 1.06 | |
| 1.02 | 1.02 |
| 0.99 | |
| 0.95 | |
| 0.93 | |
| 0.92 | |
| CODE: | 024205 |
| Formula: | TlClO4 |
| d-value | match |
| 4.45 | |
| 3.85 | 3.82 |
| 2.73 | 2.73 |
| 2.72 | 2.73 |
| 2.32 | |
| 2.22 | 2.22 |
| 1.93 | 1.93 |
| 1.77 | |
| 1.72 | 1.72 |
| 1.57 | 1.57 |
| 1.48 | |
| 1.36 | |
| 1.3 | |
| 1.28 | |
| 1.22 | 1.21 |
| 1.18 | |
| 1.16 | |
| 1.11 | |
| 1.08 | |
| 1.07 | |
| 1.03 | 1.02 |
| 1 | |
| 0.96 | |
| 0.94 | |
| 0.93 | |

The instant invention allows the use of the reduced unit cell parameters instead of the more common procedure of using the full symmetry unit cell results in calculating d-spacings produced by double diffraction in addition to those produced by normal diffraction. Also, no d-spacings observable in any experimental electron diffraction pattern are missing from among the d-spacings in the database and no extra d-spacings are present in the database that are not possible to be observed in electron diffraction.

The prior art does not utilize reduced unit cells in this manner and has resulted in either unmatched experimental d-spacings or nonrigorous addition of incorrect d-spacings to the experimental set.

The practice of the present invention allows use of a commercially available database management system such as Microsoft ACCESS 97.

The prior art depends on unique and inflexible search/match computer code or manual searches of printed data. The use of a common database tool allows customized extensions which can include other specific information particular to each search problem. The prior art is inflexible in this respect.

Additionally, the use of experimental error limits and number of required d-spacing matches greatly reduces the number of potential solutions to examine manually in the two output tables compared to prior art. Also, the production of output in two relational database tables permits further sorting, filtering, reformating, exporting (in a variety of common formats), or reporting, using common desktop computing tools. The prior art has no such provisions.

In the present invention, the ranking of candidate materials is done according to a new Figure of Merit, FOM, where FOM=(Matching d-spacings in the database)−(missing d-spacings in the database range of the input), (Equation 3) in the output tables results in candidate materials found at the top of the output tables being the most likely actual material or materials in the sample. As a result, the time required to interpret an electron diffraction pattern of rings by the methods and procedures of this invention is generally much less than that of other computer techniques, especially those of the NIST/Sandia/ICDD Electron Diffraction Database.

Accordingly, the known materials which are in the database but which are not in the final list of candidate materials are very unlikely to be the actual material or materials in the sample from which the electron diffraction pattern was obtained.

While some skills in crystallography and database management are required to construct a useful embodiment of this invention, no such skills are required to use such a useful embodiment to identify an unknown polycrystalline material. Consequently, this invention allows transmission electron microscopists who are not trained crystallographers to identify small polycrystalline samples of known materials in the database, without resorting to other techniques or references, and in a time period which is comparable to that required by experts skilled in crystallography who employ the methods and procedures of this invention and which is much less than that required by other methods and procedures.

It will be apparent from the foregoing that many other variations and modifications may be made regarding the methods described herein, without departing substantially from the essential features and concepts of the present invention. Accordingly, it should be clearly understood that the forms of the invention described herein are exemplary only and are not intended as limitations on the scope of the present invention as defined in the appended claims.

What is claimed is:

1. A method for analyzing polycrystalline electron diffraction data comprising:
   (a) creating tables within a relational database, said tables comprising Code Ring data, Formula data, and Element data; wherein said Code Ring data includes information relating to the d-spacings of polycrystalline materials, said Formula data includes information relating to the chemical formulae of said polycrystalline materials, and said Element data includes information relating to the presence of elements in said polycrystalline materials of high atomic number;
   (b) creating at least one macro for performing searches using said tables; said at least one macro including the steps of:
      i) requesting input data relating to observed d-spacings, experimental error limits, and anticipated atomic numbers of an experimental sample;
      ii) comparing said input data with the data in said tables and calculating a Figure of Merit (FOM) such that:

FOM=(matching $d$-spacings) −(missing $d$-spacings);

iii) generating at least one report listing in descending order the polycrystalline materials that have the highest FOM.

2. The method for analyzing polycrystalline electron diffraction data according to claim 1, wherein said code ring data includes reduced unit cell parameters, and said step of comparing said input data includes calculating d-spacings produced by double diffraction.

* * * * *